(12) United States Patent
Graham

(10) Patent No.: US 7,955,080 B2
(45) Date of Patent: Jun. 7, 2011

(54) METHOD AND SYSTEM FOR SINGLE TOOTH REPLACEMENT IN A GROWING INDIVIDUAL

(75) Inventor: John W. Graham, Phoenix, AZ (US)

(73) Assignee: ORMCO Corporation, Orange, CA (US)

( * ) Notice: Subject to any disclaimer, the term of this patent is extended or adjusted under 35 U.S.C. 154(b) by 356 days.

(21) Appl. No.: 11/755,183

(22) Filed: May 30, 2007

(65) Prior Publication Data

US 2007/0281280 A1 Dec. 6, 2007

Related U.S. Application Data

(60) Provisional application No. 60/809,539, filed on May 30, 2006.

(51) Int. Cl.
*A61C 8/00* (2006.01)
(52) U.S. Cl. ........................................................ 433/174
(58) Field of Classification Search .................. 433/172, 433/173, 174, 175, 176, 215
See application file for complete search history.

(56) References Cited

U.S. PATENT DOCUMENTS

| | | |
|---|---|---|
| 3,672,058 A | 6/1972 | Nikoghossian |
| 4,086,701 A | 5/1978 | Kawahara et al. |
| 4,252,525 A | 2/1981 | Child |
| 4,318,696 A | 3/1982 | Kasama et al. |
| 4,406,623 A | 9/1983 | Grafelmann et al. |
| 4,416,629 A | 11/1983 | Mozsary et al. |
| 4,431,416 A | 2/1984 | Niznick |
| 4,547,157 A | 10/1985 | Driskell |
| 4,552,532 A | 11/1985 | Mozsary |
| 4,626,214 A | 12/1986 | Artal |
| 4,693,686 A | 9/1987 | Sendax |
| 4,713,004 A | 12/1987 | Linkow et al. |
| 4,738,623 A | 4/1988 | Driskell |
| 5,344,457 A | 9/1994 | Pilliar et al. |
| 5,642,996 A | 7/1997 | Mochida et al. |
| 5,697,779 A | 12/1997 | Sachdeva et al. |
| 5,823,777 A | 10/1998 | Misch et al. |
| 5,954,504 A | 9/1999 | Misch et al. |
| 6,152,738 A * | 11/2000 | Aker .............................. 433/173 |
| 6,325,628 B1 * | 12/2001 | Morgan ........................ 433/173 |
| 6,572,373 B2 | 6/2003 | Tramonte |
| 6,626,671 B2 | 9/2003 | Klardie et al. |

(Continued)

FOREIGN PATENT DOCUMENTS

KR 534243 B 12/2005

OTHER PUBLICATIONS

U.S. Patent and Trademark Office, International Preliminary Report on Patentability in PCT Serial No. PCT/US07/69949, Feb. 13, 2009.

(Continued)

*Primary Examiner* — Cris L Rodriguez
*Assistant Examiner* — Eric Rosen
(74) *Attorney, Agent, or Firm* — Wood, Herron & Evans, L.L.P.

(57) ABSTRACT

An implant, system and method for use in replacement of a tooth. The implant can include a first threaded portion, a connecting member opposite the first threaded portion for attaching to a replacement tooth, a driver head positioned between the threaded portion and the connecting member, and a transmucosal collar disposed between the driver head and the first threaded portion.

16 Claims, 2 Drawing Sheets

U.S. PATENT DOCUMENTS

| | | | |
|---|---|---|---|
| 6,655,962 B1 * | 12/2003 | Kennard | 433/174 |
| 7,314,375 B2 | 1/2008 | Gault | |
| 2004/0006346 A1 | 1/2004 | Holmen et al. | |
| 2006/0199138 A1 * | 9/2006 | Corti et al. | 433/18 |
| 2006/0286509 A1 * | 12/2006 | Bassett et al. | 433/173 |
| 2007/0275350 A1 | 11/2007 | Hall | |

OTHER PUBLICATIONS

U.S. Patent and Trademark Office, International Search Report and Written Opinion in PCT Serial No. PCT/US07/69949, Oct. 1, 2008.

* cited by examiner

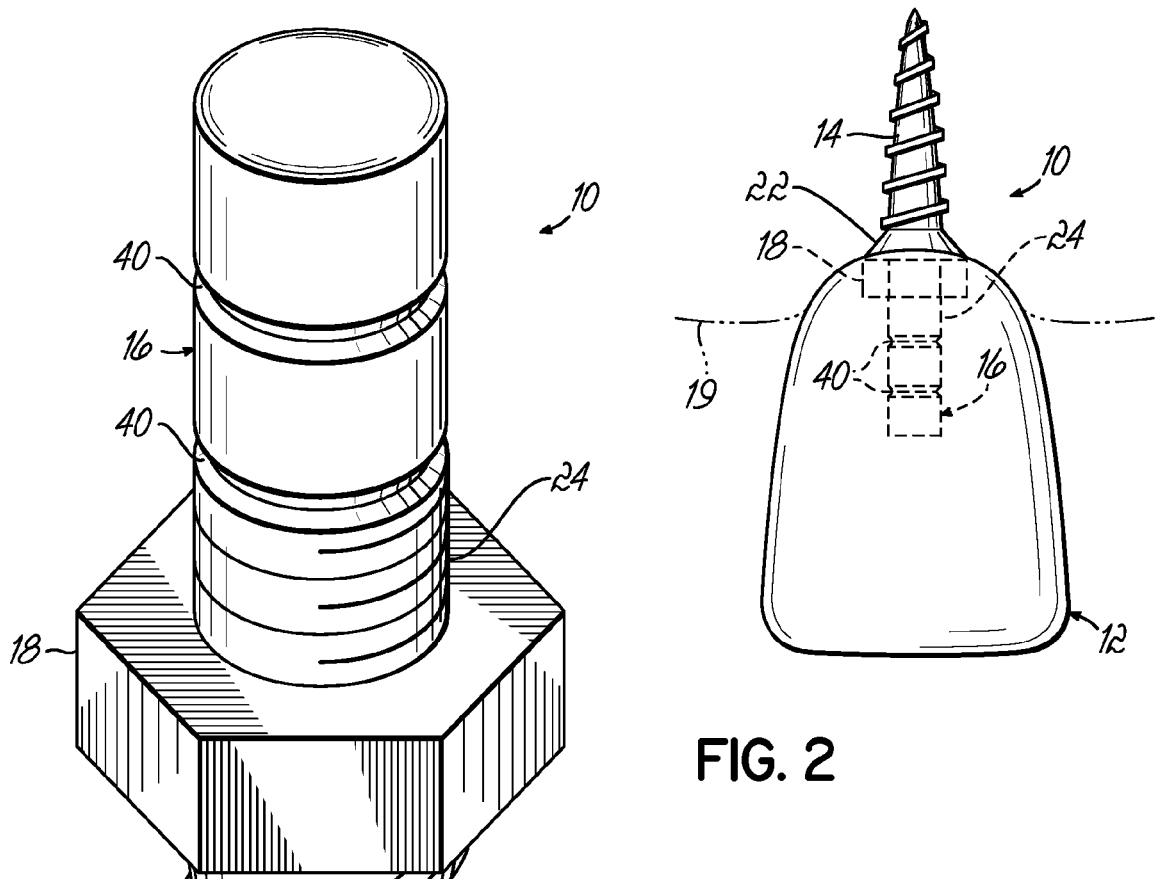
FIG. 1
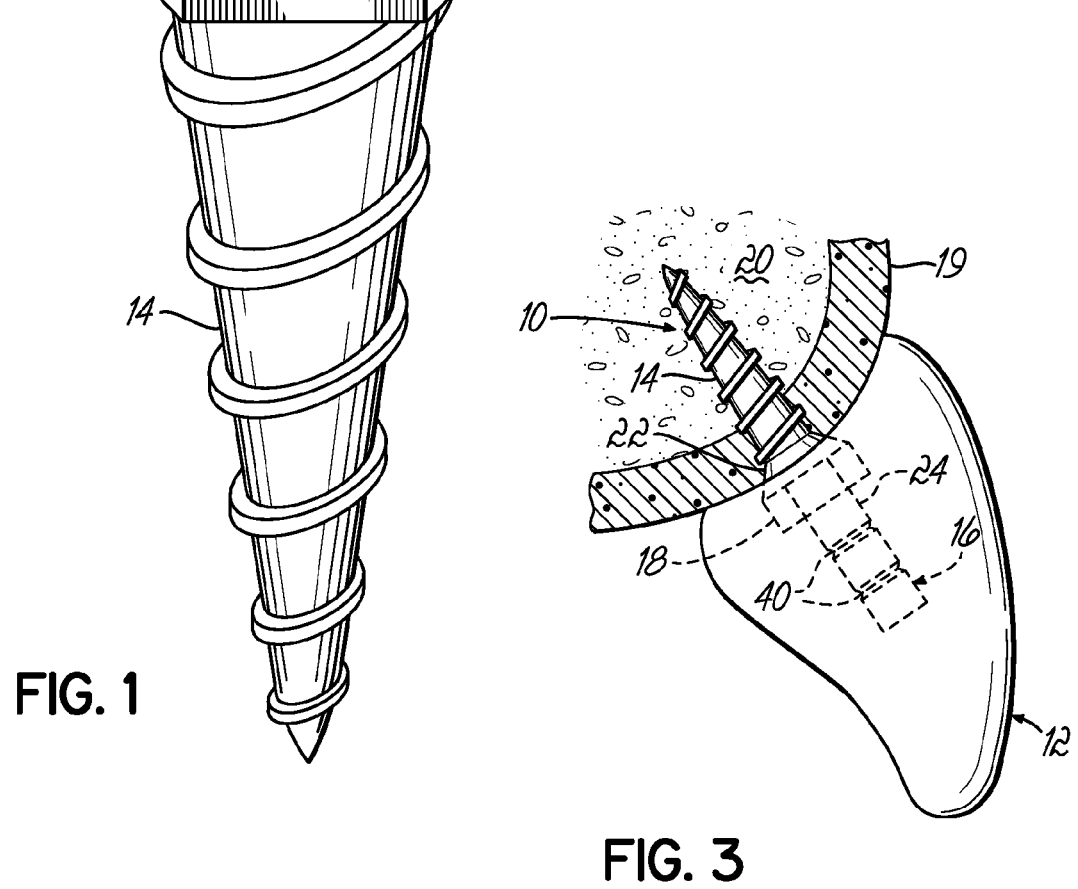
FIG. 2
FIG. 3

METHOD AND SYSTEM FOR SINGLE TOOTH REPLACEMENT IN A GROWING INDIVIDUAL

This application claims the benefit of U.S. Provisional Patent Application Ser. No. 60/809,539, filed on May 30, 2006, the disclosure of which is hereby incorporated by reference herein.

BACKGROUND

This invention generally relates to dental implants and, more particularly, to those implants used in a growing individual, such as a child or young adult.

Currently, there are limited restorative options to pursue when a growing individual is missing a maxillary or mandibular tooth, such as an anterior tooth. Such a tooth may be either congenitally missing, or missing as the result of trauma or decay. The space formed by the missing tooth may be closed orthodontically, but this option can create occlusal disharmony. For anterior teeth, aesthetic reasons would dictate the use of a dental implant. However, existing osseointegrated implants are not viable options in a growing individual because the implant remains fixed and stationary while the surrounding teeth continue to erupt. The outcome of this situation is an unacceptable aesthetic result, with significant discrepancies in the incisal edges and gingival margins.

Current options for anterior single tooth replacement in the growing individual include: fabrication and placement of a fixed partial denture (dental bridge), fabrication and placement of a removable partial denture, or some iteration of the above described options. Drawbacks to a fixed partial denture include removal of normal tooth structure of adjacent teeth, difficulty with hygiene, and unacceptable aesthetic results. Drawbacks to removable replacements include the need for removal while eating, poor aesthetics, poor fit, and potential loss of the removable appliance. Above all, the greatest drawback to either fixed or removable tooth replacement is the eventual loss of bone in the region of the missing tooth. Unless the bone in the maxillary or mandibular dental ridge is under physical load similar to a natural tooth, physiologic resorption will occur. This bone resorption establishes the need for a ridge augmentation procedure (usually a bone graft), prior to placement of an osseointegrated implant.

A need therefore exists for an improved implant, system and method for replacing a tooth, especially in a growing individual.

SUMMARY

Generally, the invention provides an implant for use in securing a replacement tooth in a patient. The implant comprises an implantable portion adapted to be secured within maxillary or mandibular bony tissue of the patient and formed to prevent osseointegration thereof. A connecting member is positioned opposite the implantable portion for receiving the replacement tooth. A driver head is disposed between the implantable portion and the connecting member. The driver head is sized and shaped for receiving a driver for driving the implantable portion into the bony tissue.

In another more particular aspect of the invention, the implant is in the form of a miniscrew and the implantable portion comprises a first threaded portion. The connecting member is located opposite the first threaded portion for receiving the replacement tooth. The driver head is disposed between the first threaded portion and the connecting member. The first threaded portion is formed in a manner that will prevent osseointegration thereof with the bony tissue.

In another aspect, a transmucosal collar may be disposed between the driver head and the first threaded portion.

The connecting member may include a second threaded portion for receiving mating threads of an attachment structure associated with the replacement tooth. The connecting member may include one or more peripheral grooves. Such grooves would be adapted to facilitate at least one of: shortening the connecting member for length adjustment, or coupling with the replacement tooth. A bonding pad may be coupled to the connecting member, with the bonding pad adapted to be secured to the replacement tooth. The connecting member may include a second threaded portion and the bonding pad may further include attachment structure having mating threads adapted to be threaded to the second threaded portion. In other embodiments attachment structure may be more directly associated with the replacement tooth. The first threaded portion may be formed to prevent osseointegration. The transmucosal collar may further comprise a flared portion transitioning from a smaller diameter to a larger diameter in a direction from the first threaded portion toward the driver head.

In another aspect, a dental implant system is provided and may include an implant having any of the features discussed herein in combination with a replacement tooth.

In another aspect, the invention provides a method for implanting a replacement tooth in a patient using an implant including an implantable portion and a connecting member. The method includes inserting the implantable portion of the implant into a maxillary or mandibular bone of the patient leaving the connecting member exposed. A replacement tooth is attached to the connecting member. Integration of bone tissue into the implantable portion is prevented.

In practicing the method, the connecting member may include a threaded portion and the method may further comprise threading an attachment structure associated with the replacement tooth onto the threaded portion. The connecting member may include at least one peripheral groove, and the method may further comprise at least one of: shortening the connecting member by removing a proximal portion of the connecting member at the peripheral groove, or coupling the replacement tooth to the connecting member using the peripheral groove. Attaching the connecting member to the replacement tooth may further comprise coupling a bonding pad to the connecting member, and securing the bonding pad to the replacement tooth. The bonding pad may further include threads for mating with the threaded portion of the connecting member. Coupling the bonding pad to the connecting member may further comprise threading the second threaded portion to the mating threads.

The connecting member may be configured to allow at least one of rotational adjustment or lengthwise adjustment of the replacement tooth relative to the connecting member. For example, this can allow for more desirable alignment of the replacement tooth and improved aesthetics. The connecting member may be formed with any suitable shape and configuration. In one illustrative embodiment, the connecting member further comprises an abutment post, which may be at least substantially cylindrical to allow rotational and lengthwise adjustment of the replacement tooth with respect thereto. In another aspect, the connecting member may be colored to match the color of the replacement tooth. As a more specific example, the implant may further comprise a metal anodized to match the color of the replacement tooth.

BRIEF DESCRIPTION OF THE DRAWINGS

FIG. 1 is a perspective view of a miniscrew constructed in accordance with an illustrative embodiment of the invention.

FIG. 2 is a front elevational view of the miniscrew of FIG. 1 coupled with a replacement tooth and shown in an implanted position relative to a gum line of a patient.

FIG. 3 is a side elevational view of a system including the miniscrew shown in FIG. 1 and a replacement tooth in an implanted condition, showing patient anatomy including gum tissue and bone tissue in cross section.

DESCRIPTION OF THE ILLUSTRATIVE EMBODIMENTS

Figure 4:
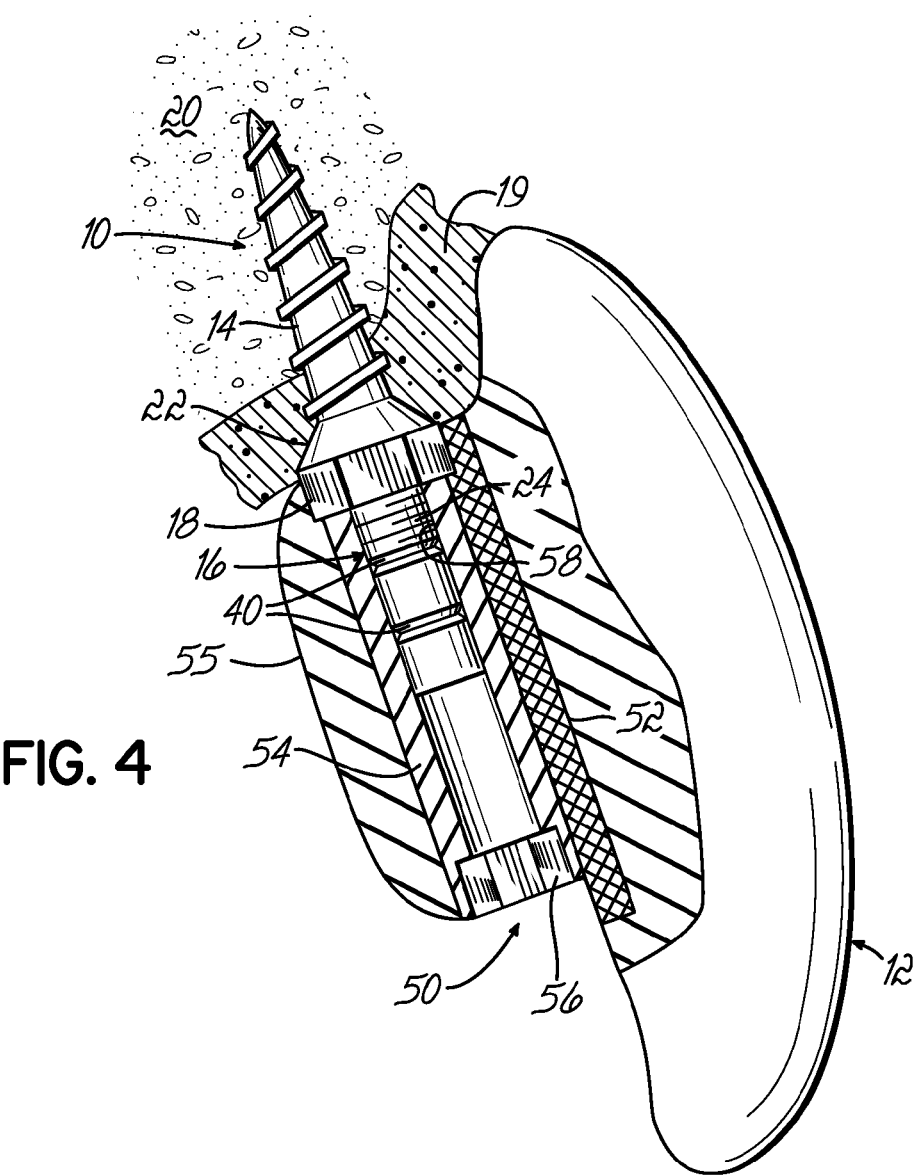
FIG. 4 is a side view, partially cross sectioned to show details of a second illustrative embodiment of a system in an implanted condition, and showing patient anatomy including gum tissue and bone tissue in cross section.

FIGS. 1-3 illustrate a first embodiment in the form of a miniscrew 10 coupled with a replacement tooth 12 (FIGS. 2 and 3). The miniscrew 10 includes a first threaded portion 14 which may comprise any one of various types of suitable thread designs, although an asymmetric buttress thread has certain advantages. An abutment post 16 is located opposite the first threaded portion 14 for attaching to the replacement tooth 12, and a driver head 18 is disposed or positioned between the first threaded portion 14 and the abutment post 16. It will be appreciated that an implant constructed in accordance with the inventive concepts herein may be formed integrally in one piece, such as by machining the miniscrew 10 out of a single piece of metal, such as titanium. Alternatively, the implant may be formed from two or more separate pieces that are assembled before or during the implantation procedure on the patient. The abutment post 16 is illustrated as being at least substantially cylindrical in shape, although in carrying various aspects of this invention, it may instead be a connecting member of any desired shape and/or configuration. The driver head 18 is sized and shaped for receiving a tool or driver (not shown) for driving the first threaded portion 14 through gingival or gum tissue 19 and into bone 20 as illustrated in FIG. 3. A transmucosal collar 22 is positioned between the driver head 18 and the first threaded portion 14. As further shown, the abutment post 16 includes a second threaded portion 24 for receiving mating threads of an attachment structure associated with the replacement tooth 12, such as on the replacement tooth itself, or on a structure that is separately attached to the replacement tooth 12 as will be described in connection with the second embodiment shown in FIGS. 4 and 5. Thus, it will be appreciated that the replacement tooth 12 may be coupled with the post 16 so as to be adjusted in a direction around the post 16 to set the appropriate rotational angle or position of the replacement tooth 12 relative to adjacent teeth, and also along the length of the post 16 to set the appropriate "eruption" position. In this latter regard, the incisal edge of the replacement tooth 12 may be aligned with the incisal edges of adjacent teeth. Once these adjustments are finalized, the replacement tooth may be fixed in position. For example, a light curable bonding agent may be applied to the post 16 and/or the associated connecting portion of the replacement tooth 12 and, after the adjustments are finalized, the bonding agent may be light cured to fix the tooth 12 at the adjusted position. Other manners of accomplishing this result will also be recognized and appreciated by those of ordinary skill in the art. The first threaded portion 14 is formed to prevent osseointegration or ingrowth of bone tissue, such as by being highly polished, treated, coated in some manner, or any combination of these or other options, to assist in preventing osseointegration. The transmucosal collar 22 is a flared or tapered section, as shown best in FIGS. 2 and 3, and is also preferably highly polished and/or treated, coated or otherwise formed to prevent tissue in-growth. In the illustrated embodiment, the flared or tapered transmucosal collar 22 flares outwardly from a smaller diameter to a larger diameter in a direction from the first threaded portion 14 toward the driver head 18. The driver head 18 is shown as a hexagonal head and the flared transmucosal collar 22 flares radially outward to a location meeting with or proximate to the outer diameter of this hexagonal driver head 18. The transmucosal collar 22 may, for example, have a length from about 1 millimeter to about 4 millimeters. The overall length of the miniscrew 10 may vary as well, but convenient lengths may be 6, 8, 9, 10 millimeters, or other lengths, depending on the needs of the particular case.

The screw 10 is preferably self-drilling and self-tapping such that placement of the screw 10 may be made directly through the gingiva 19 and into the bone 20 (FIG. 3) without the need for a pilot hole, such as through drilling, use of a tissue punch or other surgical procedure. The thread design of the asymmetric buttress thread may have a pitch in a range from about 0.6 to about 1.5 millimeters. The diameters of the miniscrews 10 may be about 1.4 millimeters to about 2.4 millimeters at the proximal or larger end of their threaded length, although other sizes are of course possible depending on needs of the user. It is contemplated that systems may be provided with two separate screws 10 associated with each implantation case to accommodate "emergency" situations. An initial screw 10 would be placed into the patient and the other screw 10 would be slightly larger in diameter and reserved for "emergency" use. Thus, if the initially placed screw 10 is damaged or becomes dislodged, then the "emergency" screw 10 may be used to replace the initial screw 10 with the larger diameter allowing for full bony engagement of the replacement "emergency" screw. As examples, if the initial screw has a diameter of 1.4 millimeters, then the associated emergency screw could have a diameter of 1.6 millimeters to 1.8 millimeters. In each case, the emergency screw may have a diameter of, for example, about 0.2 millimeter to about 0.4 millimeter larger than the initially implanted screw.

As mentioned above, the abutment post 16 may be used alone as an attachment abutment for the replacement tooth 12 or may receive a specifically designed attachment via a nut or any other manner of connection for coupling the replacement tooth 12 to the abutment post 16. In the embodiment shown in FIGS. 1-3, the abutment post 16 includes a plurality of spaced apart grooves or score lines 40. These grooves or score lines 40 may act as retentive locks or detents for the replacement tooth 12 to be bonded or otherwise connected to and/or as cutting or severing locations to allow for length adjustment of the abutment post 16 after the miniscrew 10 is placed into the patient. In this regard, the abutment post length may be shortened by using a suitable cutting tool (not shown) to cut the abutment post 16 at one of the grooves or score lines 40. Portions of the miniscrew 10, or the entire miniscrew 10 may be anodized or colored in any fashion that will, for example, prevent the miniscrew 10 from detracting from the aesthetics of the replacement tooth 12. For example, all or part of the miniscrew 10 may be colored to match the color of the replacement tooth, e.g., a shade of white. To facilitate this, the miniscrew 10 may be formed of metal such as titanium or stainless steel and an anodizing process may be used to impart the desired color to the outer surface of the miniscrew 10.

Figure 5:
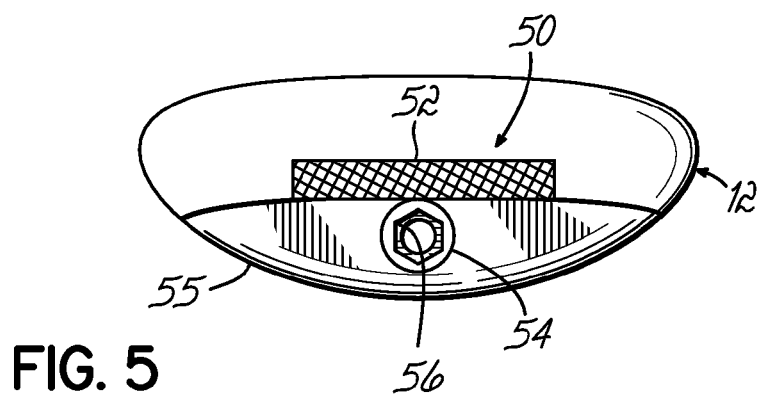
FIG. 5 is a bottom view of the system shown in FIG. 4.

FIGS. 4 and 5 illustrate another embodiment of a system including a miniscrew 10 as described in connection with FIGS. 1-3 and a replacement tooth 12. In this embodiment, an attachment structure 50 is associated with the replacement tooth 12 in the form of a bonding pad 52 and a threaded connector 54. Like numerals in FIGS. 1-5 refer to like elements as between these two different embodiments and, therefore, these elements need no further description. The threaded connector 54 is specifically in the form of a cylinder having a drive portion 56, such as a hex drive, at a proximal end and an internally threaded portion 58 at a distal end connecting with the second threaded portion 24 of the miniscrew 10. The bonding pad 52 is suitably coupled or fixed to the connector 54 and also bonded or otherwise fixed to the replacement tooth 12. Additional aesthetic material 55 may be utilized in a generally surrounding fashion relative to the connector 54 so as to obscure the connector 54 and improve overall aesthetics. In this embodiment, for example, the miniscrew 10 may be placed into bony engagement with the bone tissue 20 of the patient as previously described. The connector 54 and attached bonding pad 52 may then be fixed to the abutment post 16 by engaging the mating threads 24, 58 through rotation of the connector 54 using a suitable driver tool (not shown) engaged with the drive portion 56. The replacement tooth 12 may be bonded or otherwise fixed to the bonding pad 52 before or after this point in the procedure. Any appropriate and known dental adhesive may, for example, be used for purposes of bonding the replacement tooth 12 to the bonding pad 52. The bonding pad 52 and cylinder 54, or any other connectors used in practicing this embodiment, may also be anodized or colored in any manner that is suitable to facilitate aesthetics.

Various other components that may be included in a system for carrying out embodiments of this invention include a color shade guide and an array of replacement teeth which correspond with the shade guide. One or more bonding agents may be provided for facilitating the bonding of the replacement tooth to the abutment post 16 or other attachment structure. The system may include a driver for placement and removal of the miniscrew and/or for placement and removal of the attachment structure associated with the replacement tooth. A cutting tool may be provided for shortening the abutment post as described above. The system may be packaged to include an initial set of miniscrews and all needed armamentarium. The miniscrews 10, bonding pads 52 and individual replacement teeth 10 may be packaged in sterile conditions in any desired manner, and any other necessary written material and other audio or video instructional material may be provided as well.

It will be appreciated that the invention provides a simply, reliable system which is aesthetic and helps maintain bone tissue in the area of the missing tooth. The system comprised of the miniscrew 10 and replacement tooth 12 may be maintained in the edentulous area until the patient's growth has terminated, at which time the miniscrew 10 and replacement tooth 12 may be removed and other permanent restorative options may be pursued, such as a traditional, osseointegrated dental implant. Should the surrounding teeth continue to erupt after placement of the miniscrew 10 and replacement tooth 12 described herein, the miniscrew 10 may be either backed out by an appropriate distance, or the attachment of the replacement tooth 12 to the abutment post 16 may be adjusted such that the replacement tooth 12 is correctly positioned with respect to the adjacent teeth. As another alternative, an initial replacement tooth 12 may be replaced with another more suitable replacement tooth 12 to accommodate the growth of the patient.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features discussed herein may be used alone or in any combination depending on the needs and preferences of the user. This has been a description of illustrative aspects and embodiments the present invention, along with the preferred methods of practicing the present invention as currently known. However, the invention itself should only be defined by the appended claims.

What is claimed is:

1. A method for implanting an individual replacement tooth in a growing patient using a miniscrew including a first threaded portion and a connecting member, the method comprising:
    inserting the first threaded portion of the miniscrew into direct engagement with a maxillary or mandibular bone of the patient leaving the connecting member exposed;
    attaching the individual replacement tooth to the connecting member;
    preventing integration of bone tissue from the maxillary or mandibular bone into the first threaded portion during eruption of teeth adjacent to the individual replacement tooth; and
    adjusting the replacement tooth on the connecting member to correspond to the changing positions of adjacent teeth during eruption of the adjacent teeth.

2. The method of claim 1, wherein the connecting member includes a second threaded portion and the method further comprises:
    threading an attachment structure associated with the replacement tooth onto the second threaded portion.

3. The method of claim 1, wherein the connecting member includes at least one peripheral groove, and the method further comprises at least one of:
    shortening the connecting member by removing a proximal portion of the connecting member at the peripheral groove, or coupling the replacement tooth to the connecting member using the peripheral groove.

4. The method of claim 1, wherein attaching the connecting member to the replacement tooth further comprises:
    positioning an attachment structure including a bonding pad and a threaded connector on the connecting member,
    coupling the threaded connector to the connecting member, and
    securing the bonding pad to the replacement tooth.

5. The method of claim 4, wherein the connecting member includes a second threaded portion and the threaded connector further includes mating threads, and coupling the threaded connector to the connecting member further comprises threading the second threaded portion to the mating threads.

6. The method of claim 1, wherein the first threaded portion of the miniscrew is formed as a one-piece element.

7. The method of claim 1, wherein the first threaded portion of the miniscrew is tapered to converge in diameter in a distal direction from the connecting member.

8. The method of claim 7, wherein the first threaded portion of the miniscrew is self-drilling when inserted into direct engagement with a maxillary or mandibular bone of the patient.

9. The method of claim 1, wherein the first threaded portion of the miniscrew is self-drilling, and inserting the first threaded portion of the miniscrew into direct engagement with a maxillary or mandibular bone further comprises:

rotating the first threaded portion to self drill into the maxillary or mandibular bone of the patient without a pilot hole being drilled into the bone tissue.

10. A method for implanting an individual replacement tooth in a growing patient using an implant including an implantable portion and a connecting member, the method comprising:

inserting the implantable portion of the implant into direct engagement with a maxillary or mandibular bone of the patient leaving the connecting member exposed;

attaching the individual replacement tooth to the connecting member;

preventing integration of bone tissue from the maxillary or mandibular bone into the implantable portion during eruption of teeth adjacent to the individual replacement tooth; and adjusting the replacement tooth on the connecting member to correspond to the changing positions of adjacent teeth during eruption of the adjacent teeth.

11. The method of claim 10, wherein the implantable portion of the implant is formed as a one-piece element.

12. The method of claim 10, wherein the implantable portion of the implant is tapered to converge in diameter in a distal direction from the connecting member.

13. The method of claim 12, wherein the implantable portion of the implant is self-drilling when inserted into direct engagement with a maxillary or mandibular bone of the patient.

14. The method of claim 10, wherein the implantable portion of the implant is self-drilling, and inserting the implantable portion of the implant into direct engagement with a maxillary or mandibular bone further comprises:

rotating the implantable portion to self drill into the maxillary or mandibular bone of the patient without a pilot hole being drilled into the bone tissue.

15. A method for implanting an individual replacement tooth in a growing patient using a miniscrew including a first threaded portion with a first diameter and a connecting member, the method comprising:

inserting the first threaded portion of the miniscrew into direct engagement with a maxillary or mandibular bone of the patient leaving the connecting member exposed;

attaching the individual replacement tooth to the connecting member;

preventing integration of bone tissue from the maxillary or mandibular bone into the first threaded portion during eruption of teeth adjacent to the individual replacement tooth;

replacing the miniscrew with an emergency miniscrew having a first threaded portion with a second diameter larger than the first diameter;

attaching the replacement tooth to the emergency miniscrew; and preventing osseointegration of bone tissue from the maxillary or mandibular bone into the first threaded portion of the emergency miniscrew during eruption of teeth adjacent to the replacement tooth.

16. A method for implanting an individual replacement tooth in a growing patient using an implant including an implantable portion with a first diameter and a connecting member, the method comprising:

inserting the implantable portion of the implant into direct engagement with a maxillary or mandibular bone of the patient leaving the connecting member exposed;

attaching the individual replacement tooth to the connecting member;

preventing integration of bone tissue from the maxillary or mandibular bone into the implantable portion during eruption of teeth adjacent to the individual replacement tooth;

replacing the implant with an emergency implant having an implantable portion with a second diameter larger than the first diameter;

attaching the replacement tooth to the emergency implant; and preventing osseointegration of bone tissue from the maxillary or mandibular bone into the implantable portion of the emergency implant during eruption of teeth adjacent to the replacement tooth.

* * * * *